United States Patent [19]

Oliver et al.

[11] 4,399,123

[45] Aug. 16, 1983

[54] FIBROUS TISSUE DRESSING OR IMPLANT

[76] Inventors: Roy F. Oliver, 33 Kilmany Rd., Wormet, Fife, Scotland; Roy A. Grant, "Glen Cottage", 34 Avon Castle, Avon Castle, Ringwood, Hampshire, England

[21] Appl. No.: 221,048

[22] Filed: Dec. 29, 1980

Related U.S. Application Data

[63] Continuation-in-part of Ser. No. 43,227, May 29, 1979, abandoned.

[30] Foreign Application Priority Data

Apr. 1, 1980 [GB] United Kingdom ............... 8010955

[51] Int. Cl.³ .................... A61K 35/12; C07G 7/00; C07G 17/00
[52] U.S. Cl. .................................. 424/95; 435/267; 435/268; 435/272
[58] Field of Search ................. 435/267, 268, 272; 424/95

[56] References Cited

U.S. PATENT DOCUMENTS 3,458,397  7/1969  Myers et al. ................... 435/268
3,551,560  12/1970  Thiele ............................. 424/95

OTHER PUBLICATIONS

Solco–Chem. Abst., vol. 86 (1977), p. 15116s.
Humphrey et al.–Immunology for Students of Medicine–3rd edit., (1970), pp. 84–89 and 537–538.
Shafer–Essentials of Histology, 14th Edit., (1946), pp. 107–111.
Bartelli et al.–Chem. Abst., vol. 76 (1972), p. 135673m.
Madoff et al.–Chem. Abst., vol. 79 (1973), p. 121829s.
Santiago–Delpin et al.–Chem. Abst., vol. 78 (1973), p. 38718p.

*Primary Examiner*—Sam Rosen
*Attorney, Agent, or Firm*—Hane, Roberts, Spiecens & Cohen

[57] ABSTRACT

A fibrous tissue preparation suitable for homo or heterotransplantation is obtained by treating mammalian fibrous tissue with a proteolytic enzyme followed, if desired, by further treatment with a carbohydrate splitting enzyme.

15 Claims, No Drawings

FIBROUS TISSUE DRESSING OR IMPLANT

This application is a continuation-in-part of patent application Ser. No. 043,227, filed May 29, 1979, now abandoned.

The present invention relates to a preparation of fibrous tissue of human or animal origin, which is suitable for homo or heterotransplantation as both a temporary dressing and a permanent repair for cutaneous wounds and soft tissue injuries, and when applied in powdered form is suitable for wound cleaning. The invention further relates to a process for preparing such fibrous tissue preparations.

In the past the clinical use of tissue preparations such as dermis, for example, has been proposed for the repair of soft tissue injuries such as torn tendons, hernias and retroversion of the uterus. In dogs, plaited strips of dermis have been used to replace achilles tendons and it was claimed that the tissue assumed the function and, to a major degree, the histologic characteristics of tendon in about 10 weeks. Three successful cases of hand tendon reconstruction with dermis have been reported and many other possible clinical applications discussed.

The use of buried dermis grafts to correct defective facial contours has also been reported by Eitner (1920) who obtained good corrections in two cases of sunken cheeks and found the results more permanent than using fat or fascia.

In 1929 Loewe treated 100 cases with dermis implants which included the repair of hernias, dura mater, anthroplastics of the knee, hip and elbow and recurrent dislocation of the shoulder. Also, Straatsma reported the use of this material for correcting saddle nose deformity and the use of dermis was extended to the treatment of a number of other conditions such as reinforcement for the ligaments of the knee and dislocation of the patella and temporomandibular joint.

However, in spite of the foregoing claims the use of buried dermis grafts appeared to gain little in popularity because of the possibility of the formation of epithelial cysts originating from the sweat glands, hair follicles and sebaceous glands present in the transplanted dermis. As well as cyst formations, implantation of whole dermis often resulted in foreign body reactions and the appearance of giant cells in the implanted tissue.

In all the cases mentioned so far, the implanted dermis was taken from another site in the same individual; in other words, autogenous tissue was used.

Homotransplantation from one individual to another of the same species or heterotransplantation between individuals of different species was not attempted since whole tissue transplants, except in the case of identical twins, invariably result in immunological rejection reactions and destruction of the transplanted tissue.

We have now found that the fibrous tissue of human or animal origin which is derived from dermis, ligament, tendon, areolar tissue, basement membrane or dura mater, can be purified so that all cellular elements such as sweat glands, sebaceous glands and vascular tissue are removed, thus eliminating cyst formation and foreign body reactions when subsequently implanted into animals. The purification procedure does not significantly affect the mechanical strength of the fibrous tissue and hence the utility of the purified fibrous tissue for the repair of injuries is not impaired.

We have found unexpectedly that the resulting fibrous protein or fibroelastic tissue preparations have low or absent antigenicity, and when homografted between individuals of the same species or heterografted between individuals of a different species, do not elicit immunological rejection reactions or foreign body reactions. This is an important finding in practical terms since it means that fibrous tissue preparations taken from animals may be used to repair cutaneous or soft tissue injuries in humans.

According to one aspect of the present invention, there is provided a fibrous tissue preparation of human or animal origin which is suitable for heterotransplantation as a temporary dressing for cutaneous wounds and soft tissue injuries, which preparation is substantially free of nonfibrous tissue proteins and is substantially free of antigenic polysaccharides, mucopolysaccharides and glycoproteins.

According to another aspect of the present invention, there is provided a substantially nonantigenic fibrous tissue preparation of human or animal origin which is suitable for heterotransplantation as a permanent repair for cutaneous wounds and soft tissue injuries, which preparation is substantially free of nonfibrous tissue proteins and is substantially free of antigenic polysaccharides, mucopolysaccharides and glycoproteins. This fibrous tissue preparation is capable of being infiltrated and colonized by the host cells of another individual of the same or different species, revascularized and, in some cases, reepidermalized to form a permanent repair for cutaneous wounds and soft tissue injuries.

According to a further aspect of the present invention there is provided a novel process for treating suitable fibrous tissue of human or animal origin, such as areolar tissue, basement membrane or dura mater to render them suitable for homo or heterotransplantation. Preferably, the animals providing the fibrous tissues are mammals and, more preferably, the mammals are humans and pigs. The process comprises treating the fibrous tissue with two enzymes, one of said enzymes being a proteolytic enzyme which will, under the conditions of the process, remove nonfibrous tissue proteins, and the other of said enzymes being a carbohydrate-splitting enzyme, which will, under the conditions of the process, remove antigenic polysaccharides, mucopolysaccharides and glycoproteins from the tissue.

The order in which the enzymes are used in the process is not critical. However, if the enzymic treatment is carried out in two steps and the first of these steps is the treatment of the tissue with the proteolytic enzyme, it is then usually necessary, because the carbohydrate-splitting enzyme is a protein, to remove the proteolytic enzyme, usually by washing, from the treated tissue before proceeding to the carbohydrate removing step. Alternatively, the treatment may be carried out in the presence of both the enzymes. If it is, then the process conditions must be so chosen that when one of the enzymes is active, the other is inactive. As is well known in the art, this is normally achieved by regulating the pH.

Any proteolytic enzyme which, under the conditions of the process, will remove nonfibrous tissue proteins can be used. Suitable proteolytic enzymes include ficin, pepsin, trypsin, chymotrypsin, papain, and the like, with trypsin being preferred. We have found that above 20° C. the treatment results in an alteration of the fibre structure leading to a lower physical strength. Moreover, low temperatures discourage the growth of microorganisms in the preparation. It is therefore preferred to carry out the treatment at a temperature below 20° C. Moreover, trypsin is more stable below 20° C. and lower amounts of it are required. Generally, for the removal of antigenic protein material, it is necessary to treat the dermis or other fibrous tissue for a period of 48 hours or longer, preferably in the presence of an antiseptic and a buffer solution to maintain the correct pH.

In the case of transplants between individuals of the same species, fibrous tissue prepared from certain structures such as arterial walls may contain large amounts of mucopolysaccharides such as hyaluronic acid and also polysaccharides. While within a species such carbohydrate material may not be significantly antigenic, nevertheless it does not contribute to the strength of the tissue and may severely obstruct the subsequent recolonization of the graft by host cells such as fibroblasts and interfere with the formation of new capillaries within the graft. Also in the case of zenografts or transplants between individuals of different species, residual carbohydrate may give rise to foreign body reactions and infiltration of the graft by lymphocytes. In order to eliminate the possibility of these adverse effects, the tissue may be treated with carbohydrate-splitting enzymes. While any carbohydrate-splitting enzyme which, under the conditions of the process, will remove antigenic polysaccharides, mucopolysaccharides and glycoproteins from the tissue can be used, the preferred carbohydrate-splitting enzymes are amylase, hyaluronidase, and neuraminidase.

The amount and composition of mucopolysaccharides found in animal tissues is very variable, and while they normally only contain small amounts, arteries may contain a greater percentage. Moreover, compared with glycoproteins, mucopolysaccharides are less antigenic and some may be nonantigenic. Proteolytic enzyme treatment splits glycoproteins into carbohydrates and peptides which rapidly defuse out of the tissue. Hence, when only small amounts of mucopolysaccharides are present and where they are not demonstrably antigenic, then it may not be necessary to treat the tissue with a carbohydrate-splitting enzyme. A single-enzyme treatment with the proteolytic enzyme will provide a preparation which, after its sterilization, is suitable for implantation.

Accordingly, the present invention provides, in one aspect, a process for treating fibrous tissue of human or animal origin to provide a fibrous tissue preparation which, after its sterilization, is suitable for homo or heterotransplantation, which process comprises:
 (1) treating the fibrous tissue with a proteolytic enzyme which will, under the conditions of the process, remove nonfibrous tissue proteins and glycoproteins from the tissue; and
 (2) treating said treated fibrous tissue with a carbohydrate-enzyme to remove polysaccharides and mucopolysaccharides. If, as discussed above, the amounts of polysaccharides and mucopolysaccharides present in the fibrous tissues are small, the second step may be omitted.

We have also found that any residual antigenicity in the tissue can be removed therefrom by reacting it with a crosslinking agent which will, under the conditions of the process, form a link between the terminal amino groups of lysine groups in the tissue. The preferred crosslinking agents are glutaraldehyde, formaldehyde and nitrous acid.

This further treatment acts specifically to block the cellular immune response in heterografted fibrous tissue, i.e., grafts between individuals of different species. This blocking action is well demonstrated by the finding that purified human fibrous tissue implanted in rats elicited an immune response and that this response could be abolished by treatment of the human fibrous tissue with a dilute solution of glutaraldehyde before implantation. This effect is of the greatest practical importance since readily obtainable sources of suitable fibrous tissues are pig skin or bovine skin which, if rendered immunologically compatible with the human body, would be of the utmost utility in the treatment of large burns when homografting with human skin is at best a temporary expedient and does not lead to a long term repair of the injury. Optionally, prior to the first enzyme treatment the tissue is soaked in cold 0.5–1.9 M sodium chloride solution to remove soluble proteins therefrom and to reduce the amount of proteolytic enzyme required.

While glutaraldehyde appears to react with purified fibrous tissue to give a stable product, we have found by experiments involving $^{14}C$-labelled formaldehyde that the reaction with this compound is largely reversible (80–90 percent) when the treated tissue is subjected to prolonged washing with buffer or water. This indicates that only a small proportion of the reacted formaldehyde is permanently bound to the tissue and therefore able to protect it against attack by endogenous proteolytic enzymes when implanted into animals. We have also found that by treating purified fibrous tissue with a formaldehyde solution having a strength greater than 0.01% formaldehyde and by washing the thus treated tissue to remove therefrom free formaldehyde and any reversibly bound formaldehyde, there is provided a fibrous tissue preparation which, after its sterilization, will not invoke foreign body reactions and will become vascularized in a recipient.

It was noted in animal experiments that implanted purified dermal fibrous tissue was gradually dissolved at the site of implantation. This is a major disadvantage when the object of the operation is to obtain a permanent repair rather than a temporary dressing. This disintegration of the implanted material may be prevented by treatment with stabilizer prior to implantation to stabilize the tissue against the endogenous proteolytic enzymes. The preferred stabilizers are acrolein, diepoxides, dialdehyde starch, bifunctional sulphones, cyanuric chloride, glutaraldehyde and formaldehyde.

Accordingly, in a further aspect the present invention provides a process for treating fibrous tissue of human or animal origin to provide a fibrous tissue preparation which, after its sterilization, is suitable for homo or heterotransplantation, which process comprises:
 (1) treating the fibrous tissue with two enzymes, one of said enzymes being a proteolytic enzyme which will, under the conditions of the process, remove nonfibrous tissue proteins and glycoproteins from the tissue, and the other of said enzymes being a carbohydrate-splitting enzyme which will, under the conditions of the process, remove antigenic polysaccharides and mucopolysaccharides;
 (2) treating the tissue from (1) with a glutaraldehyde or formaldehyde solution having a strength or or more than 0.01%; and
 (3) washing the tissue from (2) to remove therefrom free formaldehyde or glutaraldehyde and any reversibly bound formaldehyde;

such that the resulting fibrous tissue preparation, after its sterilization, will not invoke foreign body reactions and will become vascularized in a recipient.

It is to be understood that when the amounts of polysaccharides and mucopolysaccharides present in the fibrous tissues are small, the treatment with a carbohydrate-splitting enzyme in step (1) may be omitted.

Throughout the specification, the strength of the formaldehyde or glutaraldehyde solution is calculated on a weight/weight basis.

While any strength of formaldehyde or glutaraldehyde solution about 0.01 percent can be used, it will be appreciated that the stronger the solution the more tanning of the resulting preparation will occur. For practical purposes, therefore, the upper limit is 10 percent. Preferably the formaldehyde solution has a strength of from 0.1 percent to 5 percent, more preferably 0.1 percent to 1.0 percent, and the glutaraldehyde solution from 0.01 to 1.0 percent. Moreover, a period of treatment of up to 28 days or even longer is preferred.

Generally speaking, water, normal saline, or aqueous buffer solution is used to wash the treated tissue.

The resulting fibrous tissue preparation may be sterilized using any technique which will not destroy the fibrous tissue structure.

The sterilized fibrous tissue preparation of the present invention can be used either as a temporary dressing, or as a permanent repair for cutaneous wounds and soft tissue injuries, or in powdered form as a wound cleansing agent.

For example, it could be used as a temporary dressing for a burn for which sufficient donor skin was available for autografting but where the operation had to be postponed for various reasons. In these circumstances, the material would have the advantage over conventional dressings of inhibiting the onset of wound contraction and granulation tissue formation and over homograft skin in preventing lymphocytic infiltration into the wound.

In cutaneous wounds the implanted purified fibrous tissue becomes overgrown with epidermis provided it is covered by a suitable dressing and eventually assumes the appearance of normal skin. We have also found unexpectedly that implanted purified fibrous tissue will inhibit the contraction of full thickness skin wounds which otherwise causes areas of distortion around the wound. The implantation of purified fibrous tissue into deep skin wounds resulted in a large reduction in the amount of granulation tissue formed in the wounds. Since granulation tissue is a precursor of scar tissue, one very important aspect of the use of this material is the prevention of scar formation and consequent disfigurement. This is particularly important in the case of cutaneous injuries to the head and hands.

In powdered, lyophilized form, the sterilized tissue preparation can be used as a wound cleansing agent in all forms of cutaneous injury. It readily absorbs wound exudate, bacteria and wound debris which is then washed from the wound.

The preparations of the present invention will have practical applications in various branches of surgery and veterinary medicine for the treatment of hernias, skin wounds, tendon injuries, correction of facial contours, joint defects and generally in plastic and reconstructive surgery and for the repair of soft tissues.

Stabilized purified fibrous tissue implants have been examined at various times up to 280 days after implantation with no obvious changes in structures. However, it is important that the strength of any glutaraldehyde solution used to stabilize the tissue should not exceed certain limits. In general, the strength of the glutaraldehyde solution should not exceed 0.5%. Treatment with solutions stronger than this has been found to result in hardening and loss of flexibility of the preparation associated with a persistent inflammatory reaction.

In order to make the process economical, it is desirable to recover and recycle the enzymes, particularly trypsin, when used, since these are very expensive. Recovery is as follows. After treatment of the tissue, the solution containing the enzyme is clarified by filtration and passed through a column of a suitable cellulosic ion exchange resin which removes the enzyme by absorption. The column is then washed with water and the enzyme subsequently displaced with strong (IM) buffer solution at pH 9 in a relatively small volume. The concentrated recovered enzyme solution is then diluted and used for treating a further batch of tissue. Alternatively, the filtered enzyme solution may be concentrated by ultra filtration before reuse.

In order to verify the lack of antigenicity in the fibrous tissue, this was implanted subcutaneously in rats and biopsied at various times after implantation. The implants which were all recovered intact became recellularized and revascularized with no overt signs of lymphocytic infiltration. The non-antigenicity was further confirmed by sensitizing rats to whole dermis plus epidermis by making implants two and four weeks before implantation of purified fibrous tissue from the same donor. The implants which were recovered at intervals up to forty weeks after operation showed no differences to those implanted in nonsensitized animals with no evidence of lymphocytic infiltration.

The purified fibrous tissue appears to be quite stable and can be stored either deep frozen or freeze-dried and can be sterilized with chemicals or gamma rays.

When implanted, the fibrous tissue becomes rapidly incorporated in the tissues and becomes vascularized and recolonized by host cells such as fibroblasts.

The invention will be more fully understood by reference to the following examples. These examples are given by way of reference only and are not to be considered as limiting.

EXAMPLE 1

Human dermis was treated with a solution of crystalline trypsin (Koch-Light) at a concentration of 2 mg/ml in 0.1 M phosphate buffer at pH 9.0 with 0.5 mg/ml sodium azide as a bactericide at 15° C. for 28 days. The partially purified fibrous tissue was thoroughly washed in saline to remove trypsin and placed in a solution of bacterial $\alpha$-amylase for one hour at 15° C. followed by thorough rinsing in saline. The material was then placed in a solution of 0.01% glutaraldehyde in Tris buffer pH 7.2 for 16 hours at 15° C. followed by a further washing with saline. The resulting preparation was implanted subcutaneously in hooded Porton rats (strain PVG/C). The implanted preparation became infiltrated with host fibroblasts and revascularized. There was no evidence of lymphocytic infiltration foreign body reactions or giant cell formation in the implanted material.

EXAMPLE 2

The procedure of Example 1 was repeated but a solution of chymotrypsin was used in place of the solution of crystalline trypsin. Essentially, the same results were obtained.

EXAMPLE 3

The procedures of Example 1 was repeated with tendons from rats replacing the human dermis tissue. The tendons were ground before treatment. The final preparation gave the same results as obtained with the preparation of Example 1.

EXAMPLE 4

The procedure of Example 1 was repeated using ligament from pigs in place of the human dermis tissue. The ligament was ground before treatment. The final preparation gave the same results as obtained with the preparation of Example 1.

EXAMPLE 5

The preparation, stability both in vitro and in vivo, and resistance to bacterial collagenase of trypsin-purified pig dermal collagen cross-linked with a range of concentrations of formaldehyde in phosphate-buffered saline was studied using $^{14}C$-labelled formaldehyde as a tracer. Washing in phosphate-buffered saline at 37° C. produced rapid loss of formaldehyde over 6 weeks before stability was reached. After 19 weeks washing, 12–20% of the initial radioactivity remained representing 6 mol, 18 mol and 35 mol of formaldehyde/g of collagen after 21 days reaction with 0.1%, 1% and 5% formaldehyde respectively. Collagen incorporating stable-bound formaldehyde arising from reaction with formaldehyde in concentrations of 0.5% or over was totally resistant to bacterial collagenase.

The stabilizing effect of formaldehyde cross-linking was also demonstrated by implants of fibrous pig dermal collagen in rats. After 8 weeks a significant constant amount of formaldehyde was retained in all implants. There was no net loss of mass over a 24 week period when pre-treated with 1% formaldehyde, but some loss when pretreated with 0.1% formaldehyde.

Specific Activity of Implants

There was a loss of radioactivity from both controls and implants. Since it has already been shown that initially bound formaldehyde is lost over a period of several weeks at 37° C., this decrease in specific activity in both control and implanted collagen during the first 8 weeks was as expected. However, there was a greater decrease in the specific activity of the implants compared to the controls during this first 8 weeks. Thereafter, the specific activity of the implants remained constant and at a level of 60% and 70% of control values with 0.1% and 1% formaldehyde treated collagen respectively.

Histology of Implants

At two weeks, both the 0.1% and 1% formaldehyde treated implants showed peripheral revascularization and recellularization and by 4 weeks, the implants were cellularized throughout. The development of granulation tissue and then the deposition of new collagen occurred in the follicle cavities.

Over the first 4 weeks, mononuclear cells were present, particularly at the edges of the implants, as were occasional multi-nuclear giant cells, but by 12 weeks their presence was greatly reduced, especially in the 1% formaldehyde treated implants.

At 12 and 24 weeks, the implants showed excellent preservation of the original collagen bundle architecture with some apparent peripheral diminishment of bundle size where the implants had knitted into a thin layer of recipient connective tissue.

EXAMPLE 6

Pig dermis was treated with a solution of crystalline trypsin (Koch-Light) at a concentration of 2 mg/ml in 0.1 M phosphate buffer at pH 9.0 with 0.5 mg/ml sodium azide as a bactericide at 15° C. for 28 days. The material was then placed in a solution of 0.01% glutaraldehyde in phosphate buffer pH 9.0 for 16 hours at 15° C. and thoroughly washed in saline. The resulting preparation was implanted subcutaneously in hooded Porton rats (strain PVG/C). The implanted preparation became infiltrated with host fibroblasts and revascularized. There was no evidence of lymphocytic infiltration or foreign body reactions in the implanted material.

We claim:

1. A fibrous tissue preparation of mammalian dermal origin which is suitable for homo or heterotransplantation for the permanent repair of or as temporary dressing for cutaneous wounds and soft tissue injuries, which preparation is substantially free of nonfibrous tissue proteins and antigenic polysaccharides, mucopolysaccharides, and glycoproteins.

2. A fibrous tissue preparation according to claim 1, wherein the mammal is a human or pig.

3. A process for the preparation of a fibrous tissue according to claim 1, which comprises treating below 20° C. a fibrous tissue of mammalian origin with a proteolytic enzyme selected from the group consisting of pepsin, trypsin, chymotrypsin, ficin, and papain, which will, under the conditions of the process, remove nonfibrous tissue proteins, and further treating said fibrous tissue with a carbohydrate-splitting enzyme, selected from the group consisting of amylase, hyaluronidase, and neuramidinase, which will, under the conditions of the process, remove antigenic polysaccharides, mucopolysaccharides and glycoproteins from said fibrous tissue.

4. A process according to claim 3 in which the fibrous tissue is treated with both the proteolytic and carbohydrate-splitting enzymes, wherein substantially all of the proteolytic enzyme is removed from said fibrous tissue before treating said fibrous tissue with the carbohydrate-splitting enzyme.

5. A process according to claim 3, wherein the proteolytic enzyme is trypsin.

6. A process according to claim 3, wherein prior to the first enzyme treatment the fibrous tissue is contacted with a cold aqueous sodium chloride solution.

7. A process according to claim 3 which further comprises the step of treating the fibrous tissue with a cross-linking agent, selected from the group consisting of glutaraldehyde, formaldehyde, or nitrous acid, which forms a link between the terminal amino groups of the lysine groups in the fibrous tissue, and under the conditions of the process removes any antigenicity from the tissue.

8. A process according to claim 7 wherein the further treatment with the cross-linking agent comprises:
   (1) treating the tissue with a formaldehyde or glutaraldehyde solution having a strength of more than 0.01% by weight; and
   (2) washing the tissue to remove therefrom free formaldehyde, any reversibly bound formaldehyde, and free glutaraldehyde;

such that the resulting fibrous tissue preparation, after its sterilization, will not invoke foreign body reactions and will become vascularized in a recipient.

9. A process as claimed in claim 8, in which the fibrous tissue is treated with said proteolytic enzyme, and, before the fibrous tissue is treated with said carbohydrate-splitting enzyme, all or substantially all, of said proteolytic enzyme is removed therefrom.

10. A process as claimed in claim 9, in which the fibrous tissue is treated in the presence of both enzymes, the process conditions being so chosen that when one of said enzymes is active, the other is inactive.

11. A process as claimed in claim 8, in which said formaldehyde solution has a strength of more than 0.01% and not more than 10%.

12. A process as claimed in claim 8, in which said glutaraldehyde solution has a strength of from 0.1% to 1.0%.

13. A fibrous tissue preparation which has been provided by the process of claim 7.

14. A fibrous tissue preparation which has been prepared by the process of claim 8.

15. A tissue preparation which is suitable as a cleansing agent for cutaneous wounds and soft tissue injuries and which has been provided by sterilizing, lyophilizing and powdering a fibrous tissue preparation as claimed in claim 14.

* * * * *